(12) United States Patent
Ikeda et al.

(10) Patent No.: US 9,173,555 B2
(45) Date of Patent: Nov. 3, 2015

(54) ENDOSCOPE

(75) Inventors: Toshiyuki Ikeda, Kanagawa (JP); Kan Naito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 266 days.

(21) Appl. No.: 13/158,230

(22) Filed: Jun. 10, 2011

(65) Prior Publication Data

US 2011/0306838 A1  Dec. 15, 2011

(30) Foreign Application Priority Data

Jun. 11, 2010 (JP) ................................ 2010-134014

(51) Int. Cl.
| | |
|---|---|
| A61B 1/04 | (2006.01) |
| A61B 1/12 | (2006.01) |
| A61B 1/06 | (2006.01) |
| A61B 1/00 | (2006.01) |
| A61B 1/005 | (2006.01) |
| A61B 1/018 | (2006.01) |
| A61B 1/05 | (2006.01) |

(52) U.S. Cl.
CPC ............. *A61B 1/126* (2013.01); *A61B 1/00091* (2013.01); *A61B 1/0051* (2013.01); *A61B 1/018* (2013.01); *A61B 1/05* (2013.01); *A61B 1/0669* (2013.01)

(58) Field of Classification Search
USPC ................. 600/121–125, 127–130, 109–113, 600/155–181
See application file for complete search history.

(56) References Cited

U.S. PATENT DOCUMENTS

| | | | | |
|---|---|---|---|---|
| 2004/0158129 A1* | 8/2004 | Okada et al. | ................... | 600/168 |
| 2007/0260118 A1 | 11/2007 | Otawara | ........................ | 600/129 |
| 2008/0086032 A1 | 4/2008 | Ichimura | ........................ | 600/156 |
| 2008/0200764 A1* | 8/2008 | Okada | ........................... | 600/157 |
| 2009/0253966 A1 | 10/2009 | Ichimura | ........................ | 600/175 |

FOREIGN PATENT DOCUMENTS

| | | |
|---|---|---|
| CN | 101098655 A | 1/2008 |
| JP | 3-165731 A | 7/1991 |
| JP | 2000-234882 A | 8/2000 |
| JP | 2003-210388 A | 7/2003 |

(Continued)

OTHER PUBLICATIONS

"Presentation of Publications or the Like" dated Jan. 17, 2013 with English translation.
Notification of Reasons for Rejection dated Nov. 15, 2013 with partial English translation.
U.S. Office Action dated Mar. 25, 2014 for co-pending related U.S. Appl. No. 14/093,446.

(Continued)

*Primary Examiner* — Ryan Henderson
(74) *Attorney, Agent, or Firm* — McGinn IP Law Group, PLLC

(57) ABSTRACT

Provided is an endoscope which is capable of letting a liquid drain off to a satisfactory level at the time of cleaning, while securing the degree of freedom of a layout. An observation window is placed on an observation window base part which is formed on a distal end surface of a distal end part so as to protrude from the surrounding area. An outer peripheral shape of the observation window base part is formed into a streamline shape with respect to a flow of a cleaning fluid jetted from a nozzle. With this feature, it is possible to block a liquid flow having a low flow rate from flowing on the observation window, and to allow the liquid flow which has been used for cleaning to promptly move to the outside of the observation window.

27 Claims, 12 Drawing Sheets

(56) References Cited

FOREIGN PATENT DOCUMENTS

| | | |
|---|---|---|
| JP | 2006-187546 A | 7/2006 |
| JP | 2006-314459 A | 11/2006 |
| JP | 2006-320366 A | 11/2006 |
| JP | 2006-320367 A | 11/2006 |
| JP | 2007-209395 A | 8/2007 |
| JP | 2008-86664 A | 4/2008 |
| WO | WO 2007/091407 A1 | 8/2007 |

OTHER PUBLICATIONS

Chinese Office Action dated Jun. 4, 2014.
Notification of Reasons for Rejection dated Apr. 24, 2014 with partial English translation.
Chinese Office Action dated Dec. 31, 2014 with an English translation thereof.
Chinese Office Action dated Nov. 15, 2014 with English Translation.
United States Office Action dated Aug. 3, 2015 in U.S. Appl. No. 14/093,446.

\* cited by examiner

ENDOSCOPE

BACKGROUND OF THE INVENTION

1. Field of the Invention

The presently disclosed subject matter relates to an endoscope, and more particularly, to an endoscope in which an observation window can be cleaned by jetting a cleaning fluid from a nozzle.

2. Description of the Related Art

There has been known an endoscope including a cleaning nozzle at a distal end part thereof, in which a cleaning liquid (such as water) and a gas (such as air and carbon dioxide gas) are jetted from the cleaning nozzle toward an observation window, to thereby enable cleaning of the observation window.

Japanese Patent Application Laid-Open No. 03-165731 describes a technology concerning such an endoscope including the cleaning nozzle, in which a convex portion is provided between the observation window and the cleaning nozzle, to thereby distribute the cleaning liquid to all over the surface of the observation window.

In addition, Japanese Patent Application Laid-Open No. 2003-210388 describes a technology in which the observation window is formed so as to protrude by a predetermined amount from an end surface of the distal end part, a peripheral edge of the observation window is formed so as to be inclined, and the cleaning liquid is jetted from the cleaning nozzle toward the inclined peripheral edge of the observation window.

In addition, Japanese Patent Application Laid-Open Nos. 2006-314459, 2006-320366, 2006-320367, and 2008-86664 each describe a technology in which the end surface of the distal end part on which the observation window is placed is formed in a stepwise manner, an inclined surface is formed in a wall part between respective adjacent two steps, and the cleaning liquid is jetted from the cleaning nozzle toward the inclined surfaces.

SUMMARY OF THE INVENTION

However, in the conventional structure of the distal end part, when jetting of the cleaning liquid is stopped, liquid drops remain on the observation window to block the field of view in some cases. That is, even after an operation of stopping the jetting is performed, the cleaning nozzle cannot stop discharging the cleaning liquid immediately, and instead the jetting gradually loses its force to stop. Therefore, the cleaning liquid which is discharged around the end and has weak force cannot pass through the observation window to attach onto the observation window in some cases. In addition, in the case where switching is made from water supply to air supply, the cleaning liquid remaining inside of a tube is pushed by the gas to be discharged from the cleaning nozzle. Similarly at this time, the cleaning liquid is discharged from the cleaning nozzle without strong force, and thus attaches onto the observation window in some cases. The liquid drops attaching on the observation window in this way are removed by jetting a gas from the cleaning nozzle, and there is a disadvantage that a pressure of the supplied gas needs to be made strong in order to completely remove minute liquid drops.

In addition, in recent years, a diameter of the endoscope becomes increasingly smaller, which causes a situation where the observation window is placed in the vicinity of an outer peripheral edge of the distal end part. Normally, the outer peripheral edge of the distal end part is round-chamfered, and there are problems that the liquid drops easily attach onto such a round-chamfered portion, and that it is difficult to remove the liquid drops once attaching thereon. Accordingly, if the observation window is placed in the vicinity of the round-chamfered outer peripheral edge as described above, there is a disadvantage that the liquid drops remain on the observation window more easily.

The presently disclosed subject matter has been made in view of the above-mentioned circumstances, and therefore has an object to provide an endoscope which is capable of letting a liquid drain off to a satisfactory level at the time of cleaning, while securing the degree of freedom of a layout.

In order to achieve the above-mentioned object, a first aspect of the presently disclosed subject matter provides an endoscope including: a distal end part having a round-chamfered outer peripheral edge; an observation window on an end surface of the distal end part; a nozzle which jets a cleaning fluid toward the observation window; and an observation window base part on which the observation window is placed, the observation window which is formed on the end surface of the distal end part so as to protrude from a surrounding area, and has an outer peripheral shape formed into a streamline shape with respect to a flow of the cleaning fluid jetted from the nozzle.

According to the first aspect, the observation window is placed on the observation window base part which is formed on the end surface of the distal end part so as to protrude from the surrounding area. The outer peripheral shape of the observation window base part is formed into the streamline shape with respect to the flow of the cleaning fluid jetted from the nozzle. With this feature, it is possible to block a liquid flow having a low flow rate from flowing on the observation window, and to allow the liquid flow which has been used for cleaning to promptly move to the outside of the observation window.

In order to achieve the above-mentioned object, according to a second aspect of the presently disclosed subject matter, in the endoscope according to the first aspect, the observation window base part is formed so as to extend up to the outer peripheral edge of the distal end part along the flow of the cleaning fluid jetted from the nozzle.

In the endoscope of the second aspect, the observation window base part is formed so as to extend up to the outer peripheral edge of the distal end part. With this feature, even in the case where the observation window is placed in the vicinity of the round-chamfered outer peripheral part of the distal end part, it is possible to prevent liquid drops from remaining on the observation window.

In order to achieve the above-mentioned object, a third aspect of the presently disclosed subject matter provides an endoscope including: a distal end part having a round-chamfered outer peripheral edge; an observation window on an end surface of the distal end part; a nozzle which jets a cleaning fluid toward the observation window; and an observation window base part on which the observation window is placed, the observation window which is formed on the end surface of the distal end part so as to protrude from a surrounding area and to extend up to an outer peripheral edge of the distal end part along a flow of the cleaning fluid jetted from the nozzle.

According to the third aspect, the observation window is placed on the observation window base part which is formed on the end surface of the distal end part so as to protrude from the surrounding area. The observation window base part is formed so as to extend up to the outer peripheral edge of the distal end part along the flow of the cleaning fluid jetted from the nozzle. With this feature, even in the case where the observation window is placed in the vicinity of the round-chamfered outer peripheral part of the distal end part, it is possible to prevent the liquid drops from remaining on the observation window.

In order to achieve the above-mentioned object, a fourth aspect of the presently disclosed subject matter provides an endoscope including: a distal end part having a round-chamfered outer peripheral edge; an observation window on an end surface of the distal end part; a nozzle which jets a cleaning fluid toward the observation window; and an observation window base part on which the observation window is placed, the observation window which is formed on the end surface of the distal end part so as to protrude from a surrounding area and to extend up to an outer peripheral edge of the distal end part along a straight line which connects the nozzle with the observation window.

According to the fourth aspect, the observation window is placed on the observation window base part which is formed on the end surface of the distal end part so as to protrude from the surrounding area. The observation window base part is formed so as to extend up to the outer peripheral edge of the distal end part along the straight line which connects the nozzle with the observation window. With this feature, even in the case where the observation window is placed in the vicinity of the round-chamfered outer peripheral part of the distal end part, it is possible to prevent the liquid drops from remaining on the observation window.

In order to achieve the above-mentioned object, a fifth aspect of the presently disclosed subject matter provides an endoscope including: a distal end part having a round-chamfered outer peripheral edge; an observation window on an end surface of the distal end part; a nozzle which jets a cleaning fluid toward the observation window; and an observation window base part on which the observation window is placed, the observation window which is formed on the end surface of the distal end part so as to protrude from a surrounding area and to extend up to an outer peripheral edge of the distal end part located at a closest position from the observation window.

According to the fifth aspect, the observation window is placed on the observation window base part which is formed on the end surface of the distal end part so as to protrude from the surrounding area. The observation window base part is formed so as to extend up to the outer peripheral edge located at the closest position from the observation window. With this feature, even in the case where the observation window is placed in the vicinity of the round-chamfered outer peripheral part of the distal end part, it is possible to prevent the liquid drops from remaining on the observation window.

In order to achieve the above-mentioned object, according to a sixth aspect of the presently disclosed subject matter, in the endoscope according to any one of the third to fifth aspects, an outer peripheral shape of the observation window base part is formed so as to converge toward the outer peripheral edge of the distal end part.

In the endoscope of the sixth aspect, the outer peripheral shape of the observation window base part is formed so as to converge toward the outer peripheral edge of the distal end part. With this feature, it is possible to allow the liquid flow which has been used for cleaning to promptly move to the outside of the observation window.

In order to achieve the above-mentioned object, according to a seventh aspect of the presently disclosed subject matter, in the endoscope according to the sixth aspect, the outer peripheral shape of the observation window base part is formed so as to converge toward the nozzle.

In the endoscope of the seventh aspect, the outer peripheral shape of the observation window base part is formed so as to converge toward the nozzle. With this feature, it is possible to block the liquid flow having a low flow rate from flowing on the observation window.

In order to achieve the above-mentioned object, according to an eighth aspect of the presently disclosed subject matter, in the endoscope according to any one of the first to seventh aspects, an outer peripheral edge of the observation window base part is formed so as to be inclined.

In the endoscope of the eighth aspect, the outer peripheral edge of the observation window base part is formed so as to be inclined. With this feature, it is possible to more effectively block the liquid flow having a low flow rate, and to allow the liquid flow which has been used for cleaning to promptly move to the outside of the observation window.

In order to achieve the above-mentioned object, according to a ninth aspect of the presently disclosed subject matter, the endoscope according to any one of the first to eighth aspects further includes: an illumination window; and an illumination window base part on which the illumination window is placed, the illumination window which is formed on the end surface of the distal end part so as to protrude from a surrounding area, and has an outer peripheral shape formed into a streamline shape with respect to the flow of the cleaning fluid jetted from the nozzle.

According to the ninth aspect, the illumination window is placed on the illumination window base part which is formed on the end surface of the distal end part so as to protrude from the surrounding area. The outer peripheral shape of the illumination window base part is formed into the streamline shape with respect to the flow of the cleaning fluid jetted from the nozzle. With this feature, it is possible to block the liquid flow having a low flow rate from flowing on the illumination window, and to allow the liquid flow which has been used for cleaning to promptly move to the outside of the illumination window.

In order to achieve the above-mentioned object, according to a tenth aspect of the presently disclosed subject matter, in the endoscope according to the ninth aspect, the illumination window base part is formed so as to extend up to the outer peripheral edge of the distal end part along the flow of the cleaning fluid jetted from the nozzle.

In the endoscope of the tenth aspect, the illumination window base part is formed so as to extend up to the outer peripheral edge of the distal end part. With this feature, even in the case where the illumination window is placed in the vicinity of the round-chamfered outer peripheral part of the distal end part, it is possible to prevent the liquid drops from remaining on the illumination window.

In order to achieve the above-mentioned object, according to an eleventh aspect of the presently disclosed subject matter, the endoscope according to any one of the first to eighth aspects further includes: an illumination window; and an illumination window base part on which the illumination window is placed, the illumination window which is formed on the end surface of the distal end part so as to protrude from a surrounding area and to extend up to an outer peripheral edge of the distal end part along the flow of the cleaning fluid jetted from the nozzle.

In the endoscope of the eleventh aspect, the illumination window is placed on the illumination window base part which is formed on the end surface of the distal end part so as to protrude from the surrounding area. The illumination window base part is formed so as to extend up to the outer peripheral edge of the distal end part along the flow of the cleaning fluid jetted from the nozzle. With this feature, even in the case where the illumination window is placed in the vicinity of the round-chamfered outer peripheral part of the distal end part, it is possible to prevent the liquid drops from remaining on the illumination window.

In order to achieve the above-mentioned object, according to a twelfth aspect of the presently disclosed subject matter, the endoscope according to any one of the first to eighth aspects further includes: an illumination window; and an illumination window base part on which the illumination window is placed, the illumination window which is formed on the end surface of the distal end part so as to protrude from a surrounding area and to extend up to an outer peripheral edge of the distal end part along a straight line which connects the nozzle with the illumination window.

In the endoscope of the twelfth aspect, the illumination window is placed on the illumination window base part which is formed on the end surface of the distal end part so as to protrude from the surrounding area. The illumination window base part is formed so as to extend up to the outer peripheral edge of the distal end part along the straight line which connects the nozzle with the illumination window. With this feature, even in the case where the illumination window is placed in the vicinity of the round-chamfered outer peripheral part of the distal end part, it is possible to prevent the liquid drops from remaining on the illumination window.

In order to achieve the above-mentioned object, according to a thirteenth aspect of the presently disclosed subject matter, the endoscope according to any one of the first to eighth aspects further includes: an illumination window; and an illumination window base part on which the illumination window is placed, the illumination window which is formed on the end surface of the distal end part so as to protrude from a surrounding area and to extend up to an outer peripheral edge of the distal end part located at a closest position from the illumination window.

In the endoscope of the thirteenth aspect, the illumination window is placed on the illumination window base part which is formed on the end surface of the distal end part so as to protrude from the surrounding area. The illumination window base part is formed so as to extend up to the outer peripheral edge located at the closest position from the illumination window. With this feature, even in the case where the illumination window is placed in the vicinity of the round-chamfered outer peripheral part of the distal end part, it is possible to prevent the liquid drops from remaining on the illumination window.

In order to achieve the above-mentioned object, according to a fourteenth aspect of the presently disclosed subject matter, in the endoscope according to any one of the ninth to thirteenth aspects, an outer peripheral shape of the illumination window base part is formed so as to converge toward the outer peripheral edge of the distal end part.

In the endoscope of the fourteenth aspect, the outer peripheral shape of the illumination window base part is formed so as to converge toward the outer peripheral edge of the distal end part. With this feature, it is possible to allow the liquid flow which has been used for cleaning to promptly move to the outside of the illumination window.

In order to achieve the above-mentioned object, according to a fifteenth aspect of the presently disclosed subject matter, in the endoscope according to the fourteenth aspect, the outer peripheral shape of the illumination window base part is formed so as to converge toward the nozzle.

In the endoscope of the fifteenth aspect, the outer peripheral shape of the illumination window base part is formed so as to converge toward the nozzle. With this feature, it is possible to block the liquid flow having a low flow rate from flowing on the illumination window.

In order to achieve the above-mentioned object, according to a sixteenth aspect of the presently disclosed subject matter, in the endoscope according to any one of the ninth to fifteenth aspects, an outer peripheral edge of the illumination window base part is formed so as to be inclined.

In the endoscope of the sixteenth aspect, the outer peripheral edge of the illumination window base part is formed so as to be inclined. With this feature, it is possible to more effectively block the liquid flow having a low flow rate, and to allow the liquid flow which has been used for cleaning to promptly move to the outside of the illumination window.

According to the presently disclosed subject matter, it is possible to let a liquid drain off to a higher level at the time of cleaning, while securing the degree of freedom of a layout when a diameter of the endoscope is reduced.

DETAILED DESCRIPTION OF THE PREFERRED EMBODIMENTS

Hereinafter, preferred embodiments of an endoscope according to the presently disclosed subject matter are described in detail with reference to the attached drawings.
<First Embodiment>

Figure 1:
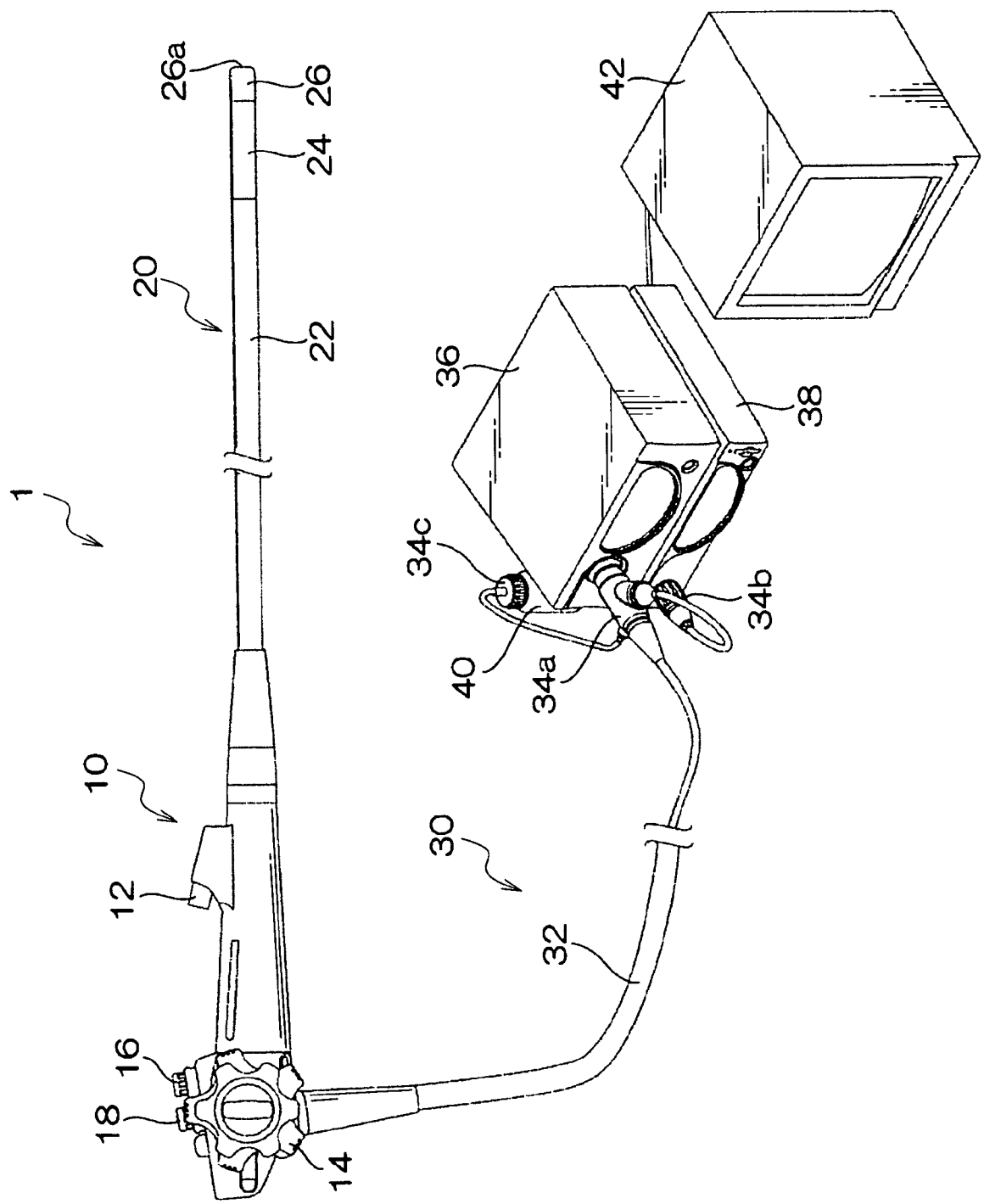
FIG. 1 is an overall configuration view illustrating an endoscope.

FIG. 1 is an overall configuration view illustrating an embodiment of the endoscope according to the presently disclosed subject matter.

An endoscope 1 is an electronic endoscope which takes out a subject image inside of a body cavity as an electronic image, and includes: an operation part 10 which is used by an operator in order to perform a required operation; an insertion part 20 which is inserted into the body cavity; and a connection part 30 for connecting with a processor apparatus and the like.

The connection part 30 includes: a universal code 32 which is provided so as to be continuous with the operation part 10; and a plurality of connectors which are provided at a distal end part of the universal code 32. These connectors are configured by: a processor connector 34A for connecting with a processor apparatus 36; a light source connector 34B for connecting with a light source apparatus 38; and an air supply/water supply connector 34C for connecting with an air supply/water supply apparatus 40.

The operation part 10 includes: a forceps entrance 12 for inserting a treatment tool; an angle knob 14 for bending a distal end of the insertion part 20 up, down, right, or left; an air supply/water supply button 16 for cleaning an observation window 50 provided at the distal end of the insertion part 20, by jetting a cleaning liquid (such as water) and a gas (such as air and carbon dioxide gas) from a nozzle 58 provided at the distal end of the insertion part 20; and a suction button 18 for suctioning from a forceps exit 56 provided at the distal end of the insertion part 20.

The insertion part 20 is formed into a tube-like shape which has a prescribed diameter and is circular in cross-section, and is integrally provided so as to be continuous with a distal end of the operation part 10. The insertion part 20 includes: a flexible part 22 having flexibility; a bendable bending part 24 provided at an end of the flexible part 22; and a distal end part 26 provided at a distal end of the bending part 24.

The flexible part 22 is made of a flexible tube, and is integrally provided so as to be continuous with the distal end of the operation part 10. A large part of the insertion part 20 is configured by the flexible part 22.

The bending part 24 is configured to be bendable, and is integrally provided so as to be continuous with a distal end of the flexible part 22. The bending part 24 bends up, down, right, or left so as to follow an operation on the angle knob 14 provided in the operation part 10. Accordingly, the distal end part 26 can be turned in a desired direction inside of the body cavity by bending the bending part 24 in the desired direction.

The distal end part 26 is formed into a columnar shape by using a hard material such as metal (for example, stainless), and is integrally provided so as to be continuous with the distal end of the bending part 24.

Figure 2:
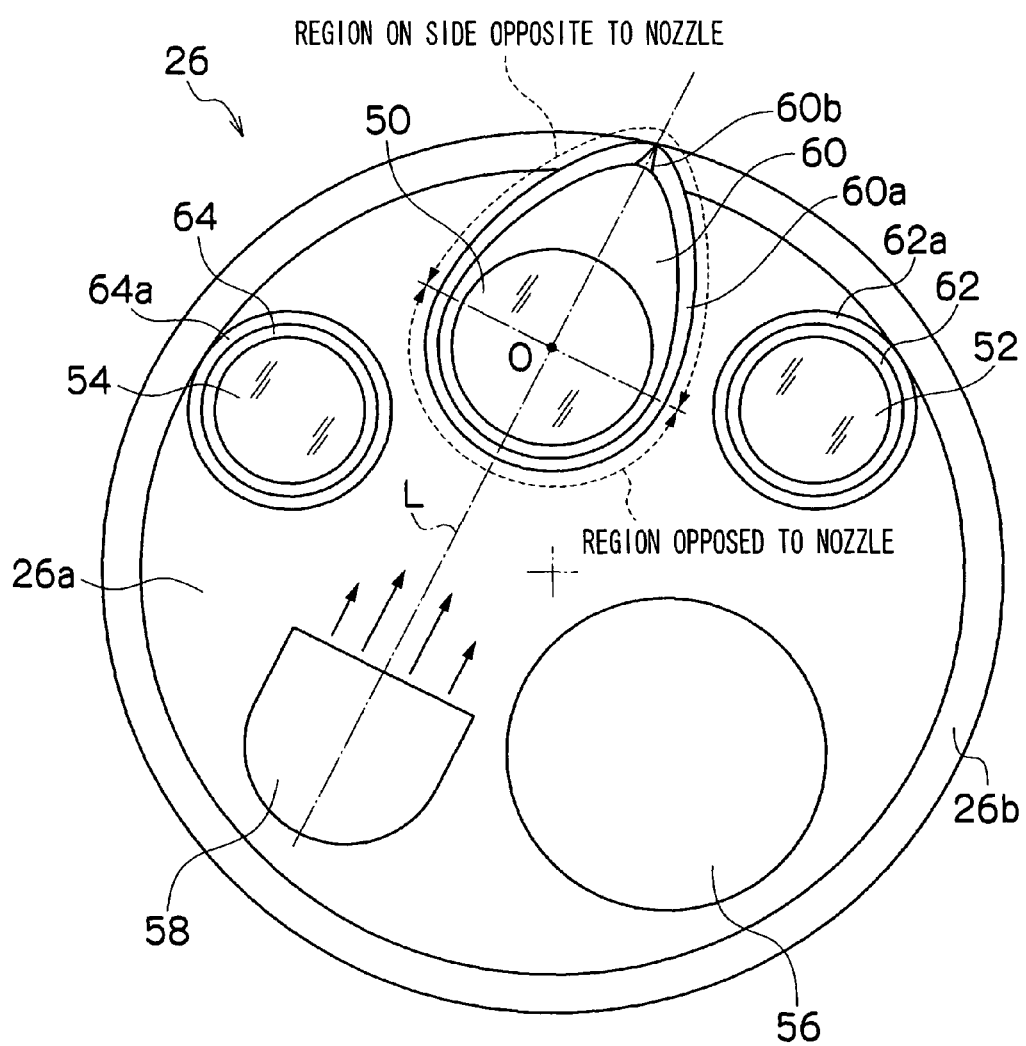
FIG. 2 is a front view illustrating a configuration of a distal end surface of a distal end part.

FIG. 2 is a front view illustrating a configuration of a distal end surface of the distal end part. As illustrated in FIG. 2, a distal end surface 26a of the distal end part 26 included in the insertion part 20 is formed into a circular shape, and the observation window 50, a pair of illumination windows 52 and 54, the forceps exit 56, and the nozzle 58 are placed on the distal end surface 26a. Particularly, in the endoscope 1 of the present embodiment, the observation window 50 is placed at a position close to an outer periphery of the distal end surface 26a, and the pair of illumination windows 52 and 54 is placed at a position close to the outer periphery thereof so as to sandwich the observation window 50. In addition, the nozzle 58 is placed so as to be opposed to the observation window 50, and the forceps exit 56 is placed adjacently to the nozzle 58. In addition, in the endoscope 1 of the present embodiment, an edge part 26b of the outer periphery of the distal end surface 26a is round-chamfered uniformly at a prescribed diameter (for example, a diameter of approximately 1.6 to 2.0 mm).

It should be noted that, although not illustrated, an objective optical system such as an objective lens is attached behind the observation window 50, and a solid-state image pick-up element (for example, CCD (Charge Coupled Device)) is attached further behind the objective optical system.

In addition, an illumination optical system is placed behind each of the paired illumination windows 52 and 54.

A light guide (not shown) provided inside of the insertion part 20 is connected to each illumination optical system. When the light source connector 34B of the connection part 30 is connected to the light source apparatus 38, this light guide is connected to a light source lamp (not shown) incorporated in the light source apparatus 38. Accordingly, when the light source lamp of the light source apparatus 38 is turned on, light emitted from the light source lamp is guided by the light guide to the illumination optical systems. Then, the lights guided by respective illumination optical systems illuminate a region to be observed through the illumination windows 52 and 54.

The objective optical system placed behind the observation window 50 receives reflected light of the light which illuminates the region to be observed through the illumination windows 52 and 54, and forms an optical image of the region to be observed on a light receiving surface of the solid-state image pick-up element. The optical image of the region to be observed which is formed on the light receiving surface of the solid-state image pick-up element is converted into an electrical signal by the solid-state image pick-up element, and is outputted to the processor apparatus 36 which is connected to the endoscope 1 via a signal line (not shown) provided inside of the insertion part 20. The processor apparatus 36 converts this electrical signal into a video signal, and outputs the video signal as an endoscopic image to the monitor 42.

The forceps exit 56 is connected to the forceps entrance 12 of the operation part 10 via a forceps channel (not shown) provided inside of the insertion part 20. A treatment tool such as a forceps which is inserted from the forceps entrance 12 protrudes from the forceps exit 56.

The nozzle 58 is provided so as to protrude from the distal end surface 26a of the distal end part 26, and includes a jet port (not shown) facing the observation window 50. An air supply/water supply channel (not shown) provided inside of the insertion part 20 is connected to the nozzle 58. The air supply/water supply channel is connected to the air supply/water supply apparatus 40 via the air supply/water supply connector 34C of the connection part 30. When the air supply/water supply button 16 provided in the operation part 10 is operated, the gas or the cleaning liquid (cleaning fluid) is selectively fed from the air supply/water supply apparatus 40 to the endoscope 1 via the air supply/water supply channel. Then, the gas or the cleaning liquid fed from the air supply/water supply apparatus 40 is fed to the nozzle 58 via the air supply/water supply channel to be jetted from the jet port of the nozzle 58 toward the observation window 50. This enables cleaning of the observation window 50.

It should be noted that the observation window 50 is cleaned by jetting the cleaning liquid from the nozzle 58. In this case, liquid drops may attach onto the observation window 50 after the cleaning. Therefore, after the cleaning, the gas is jetted from the nozzle 58, to thereby remove the liquid drops attaching on the observation window 50.

Incidentally, there is a characteristic that, if the edge part 26b of the outer periphery of the distal end surface 26a is round-chamfered as in the endoscope 1 of the present embodiment, when the observation window 50 is cleaned by the cleaning liquid, the liquid drops attach easily onto the round-chamfered edge part 26b. Then, there is a problem that, if the observation window 50 is placed in the vicinity of the edge part 26b as in the endoscope 1 of the present embodiment, in the case where the liquid drops attach onto the edge part 26b in the vicinity of the observation window 50, the field of view is blocked by the liquid drops.

In view of the above, in the endoscope 1 of the present embodiment, the distal end surface 26a of the distal end part 26 is configured in the following manner, and thus has a structure in which the liquid drops are less likely to attach onto the observation window 50 and the vicinity thereof (a structure capable of letting the liquid drain off to a satisfactory level).

As illustrated in FIG. 2, an observation window base part 60 is formed on the distal end surface 26a of the distal end part 26 so as to protrude from the surrounding area by a prescribed amount, and the observation window 50 is placed on the observation window base part 60.

The observation window base part 60 has an outer peripheral shape which is formed into a streamline shape with respect to a flow of the cleaning fluid (the cleaning liquid or the gas) jetted from the nozzle 58, and is configured in a manner that: a liquid flow having a low flow rate is prevented from flowing on the observation window 50; a liquid flow which has been used for cleaning to promptly can move to the outside of the observation window 50.

In the endoscope 1 of the present embodiment, as a specific example of the streamline shape, the observation window base part 60 is formed symmetrically to a straight line L which passes through a center O of the observation window 50 and is parallel to a flowing direction of the cleaning fluid jetted from the nozzle 58 (a jet direction of the cleaning fluid: a direction indicated by arrows in FIG. 2). Further, an outer shape of a region opposed to the nozzle 58 (a region facing the nozzle 58) is formed into a circle, and an outer shape of a region on the side opposite to the nozzle 58 (a region not facing the nozzle 58) is formed so as to extend toward the side opposite to the nozzle 58 and converge at the edge part 26b of the outer periphery of the distal end surface 26a (formed into airfoil section).

In this way, the placement region of the observation window 50 is set to the base part (observation window base part 60), and the outer peripheral shape thereof is formed into the streamline shape. Accordingly, when the liquid flow is jetted from the nozzle 58, it is possible to block the liquid flow having a low flow rate at both ends of the jet port from flowing on the observation window 50, and to allow the liquid flow to promptly move to the outside of the observation window 50. That is, it is possible to let a liquid drain off to a higher level.

Figure 3A:
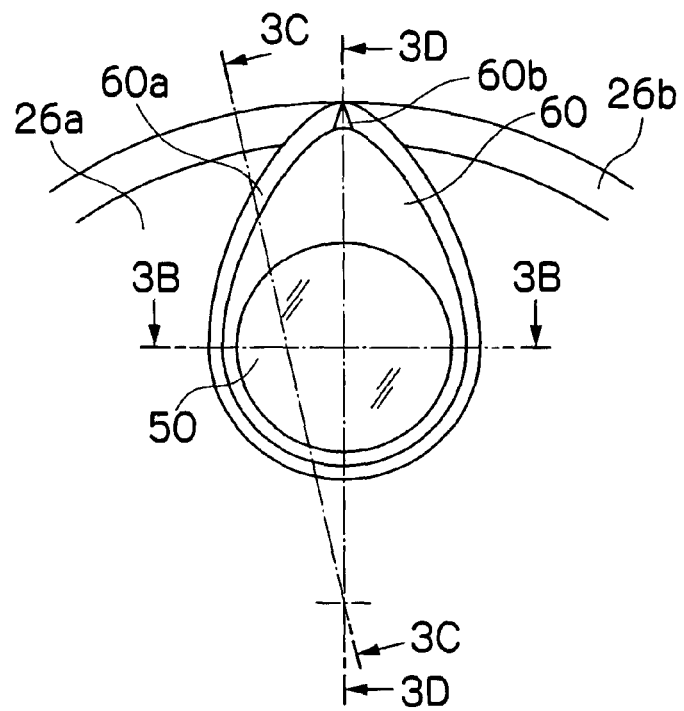
FIG. 3A is an enlarged view illustrating a main part of FIG. 2.
Figure 3B:
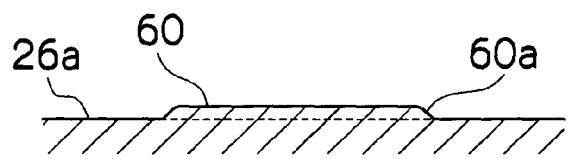
FIG. 3B is a view taken in an arrow 3B direction of FIG. 3A.
Figure 3C:
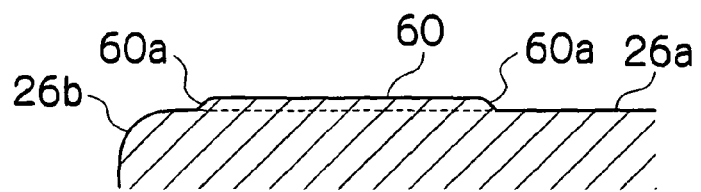
FIG. 3C is a view taken in an arrow 3C direction of FIG. 3A
Figure 3D:
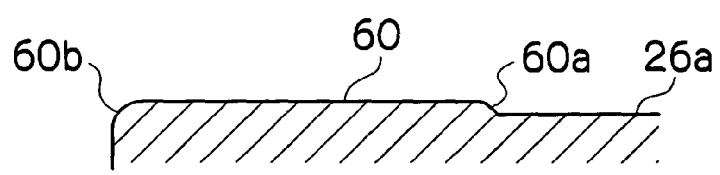
FIG. 3D is a view taken in an arrow 3D direction of FIG. 3A.

It should be noted that, in the endoscope 1 of the present embodiment, a peripheral edge part 60a of the observation window base part 60 is formed so as to be inclined at a prescribed angle (for example, 45°) as illustrated in FIGS. 3B to 3D, whereby the liquid flow is allowed to flow more smoothly on the observation window 50 and the cleaning liquid which has been used for cleaning can be discharged.

Figure 4A:
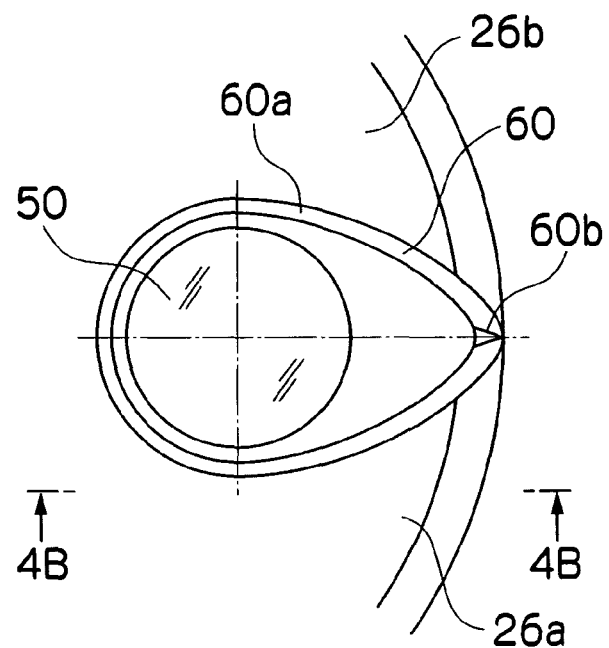
FIG. 4A is an enlarged view illustrating a main part of FIG. 2.
Figure 4B:
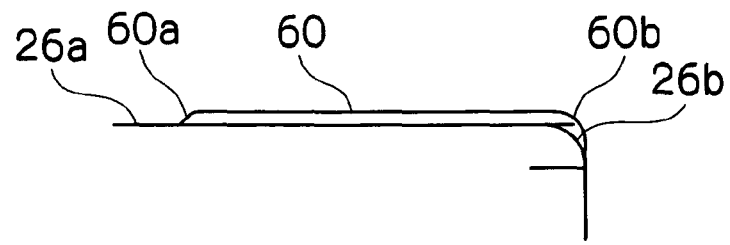
FIG. 4B is a view taken in an arrow 4B direction of FIG. 4A.

In addition, in the endoscope 1 of the present embodiment, as illustrated in FIGS. 4A and 4B, the outer shape of the region on the side opposite to the nozzle 58 is formed so as to extend up to the edge part 26b of the outer periphery on the side opposite to the nozzle 58. Then, an end part 60b at which the outer shape converges is round-chamfered at a prescribed diameter (for example, a diameter of approximately 1.0 mm). This makes it possible to reduce a stimulus to a body cavity wall.

It should be noted that, in the endoscope 1 of the present embodiment, a round-chamfering diameter (for example, a diameter of 1.0 mm) of the round-chamfered end part 60b of the observation window base part 60 is formed so as to be smaller than a round-chamfering diameter (for example, a diameter of 1.6 to 2.0 mm) of the edge part 26b of the outer periphery of the distal end surface 26a. This makes it possible to effectively prevent the liquid drops from attaching to the vicinity of the observation window 50. That is, the liquid drops have the characteristic of attaching to a round-chamfered edge part as described above, and the liquid drops tend to attach to, particularly, a region having a larger round-chamfering radius among regions which are similarly round-chamfered. Therefore, the end part 60b of the observation window base part 60 on which the observation window 50 is formed is round-chamfered at a diameter smaller than that of the edge part 26b of the outer periphery of the distal end surface 26a, whereby it is possible to effectively prevent the liquid drops from attaching to the vicinity of the observation window 50.

FIG. 3C is a cross-sectional view of the distal end part shown in FIG. 3A along the line 3C-3C. As illustrated in FIG. 3C, the peripheral edge part 60a of the observation window base part 60 is inclined with respect to the distal end surface 26a. In FIG. 3C, the inclination angle is, for example, 45 degrees, and the edge part 26b of the outer periphery of the distal end surface 26a is round-chamfered with a diameter of, for example, 2.0 mm. FIG. 3D is a cross-sectional view of the distal end part shown in FIG. 3A along the line 3D-3D drawn through the center of the distal end part and a tip of the end part 60b. In FIG. 3D, the end part 60b of the observation window base part 60 is round-chamfered with a diameter of, for example, 1.0 mm. It can be understood that, from FIGS. 3C and 3D, the edge part 60b is round-chamfered with a diameter smaller than that with which the edge part 26b of the outer periphery of the distal end surface 26a is round-chamfered.

As described above, in the endoscope 1 of the present embodiment, the observation window 50 is formed on the observation window base part 60 which protrudes from the surrounding area, and the outer peripheral shape of the observation window base part 60 extends up to the edge part 26b of the outer periphery of the distal end surface 26a to be formed into the streamline shape. This makes it possible to effectively prevent the liquid drops from attaching to the observation window 50 and the vicinity thereof. In addition, even in the case where the observation window 50 is placed in the vicinity of the edge part 26b of the outer periphery of the distal end surface 26a, it is possible to prevent the liquid drops from attaching to the vicinity of the observation window 50, and hence the degree of freedom of a layout of the observation window 50 can be increased.

It should be noted that, similarly with regard to the illumination windows 52 and 54, if the liquid drops attach thereonto, illumination performance and observation performance through the observation window 50 are deteriorated. Therefore, in the endoscope 1 of the present embodiment, the illumination windows 52 and 54 are placed respectively on illumination window base parts 62 and 64 which protrude from the surrounding area by a predetermined amount. The illumination window base parts 62 and 64 each have an outer peripheral shape which is formed into a circle corresponding to the outer peripheral shapes of the illumination windows 52 and 54, and peripheral edge parts 62a and 64a thereof are formed so as to be inclined at a prescribed angle (for example, 45°). This makes it possible to prevent the liquid flow having a low flow rate from flowing on the illumination windows 52 and 54.

<Second Embodiment>

Figure 5:
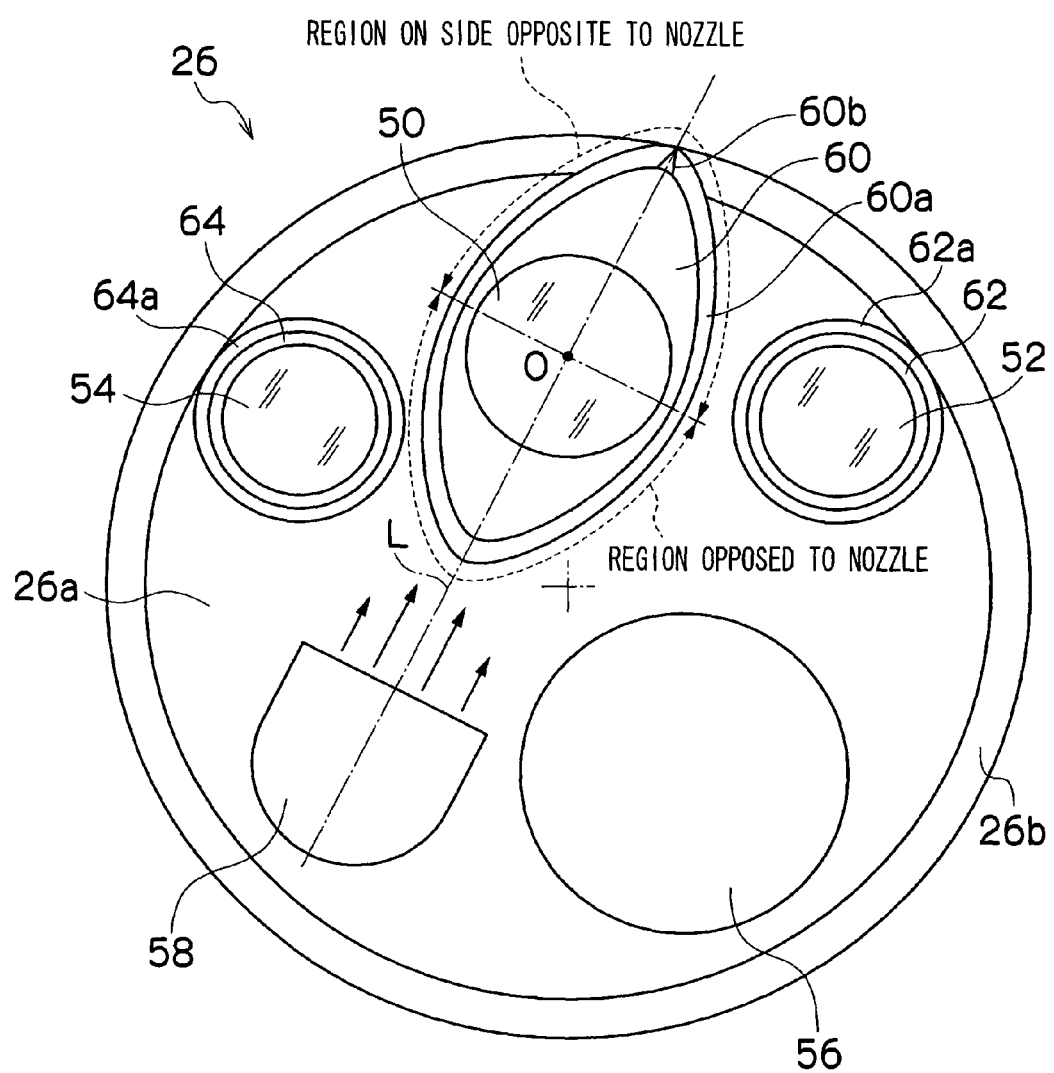
FIG. 5 is a front view illustrating a configuration of a second embodiment of the distal end surface of the distal end part.

FIG. 5 is a front view illustrating a configuration of a second embodiment of the distal end surface of the distal end part of the endoscope according to the presently disclosed subject matter.

As illustrated in FIG. 5, the endoscope of the present embodiment is different in the shape of the observation window base part 60 from the endoscope of the first embodiment. Other configuration is the same as that of the endoscope of the first embodiment, and hence only the configuration of the observation window base part 60 is described here.

As illustrated in FIG. 5, the observation window base part 60 of the endoscope of the present embodiment is also formed into a streamline shape with respect to the flow of the cleaning fluid jetted from the nozzle 58. It should be noted that, in the endoscope of the present embodiment, the outer shape of the region opposed to the nozzle 58 (the region facing the nozzle 58) is formed so as to extend toward the nozzle 58 and converge toward the center of the jet port of the nozzle 58. That is, the outer shape of the region opposed to the nozzle 58 is formed so as to extend and converge toward the nozzle 58.

On the whole, the observation window base part 60 of the endoscope of the present embodiment is the same as the observation window base part 60 of the endoscope of the first embodiment in that: the observation window base part 60 is formed symmetrically to the straight line L (the straight line which passes through the center O of the observation window 50 and is parallel to the flowing direction of the cleaning fluid jetted from the nozzle 58); the outer shape of the region on the side opposite to the nozzle 58 (the region not facing the nozzle 58) is formed so as to extend toward the side opposite to the nozzle 58 and converge at the edge part 26*b* of the outer periphery of the distal end surface 26*a*; and the peripheral edge part 60*a* is formed so as to be inclined at a prescribed angle.

In this way, the outer shape of the region opposed to the nozzle 58 is formed so as to extend toward the nozzle 58 and converge toward the center of the jet port of the nozzle 58, whereby it is possible to more effectively prevent the liquid flow having a low flow rate from flowing on the observation window 50.

It should be noted that, in the present embodiment, the outer shape of the region opposed to the nozzle 58 and the outer shape of the region on the side opposite to the nozzle 58 are formed symmetrically to each other, but do not necessarily need to be formed symmetrically to each other. It is preferable to change as appropriate the shapes thereof in accordance with a distance to the nozzle 58 and the like.

Figure 6:
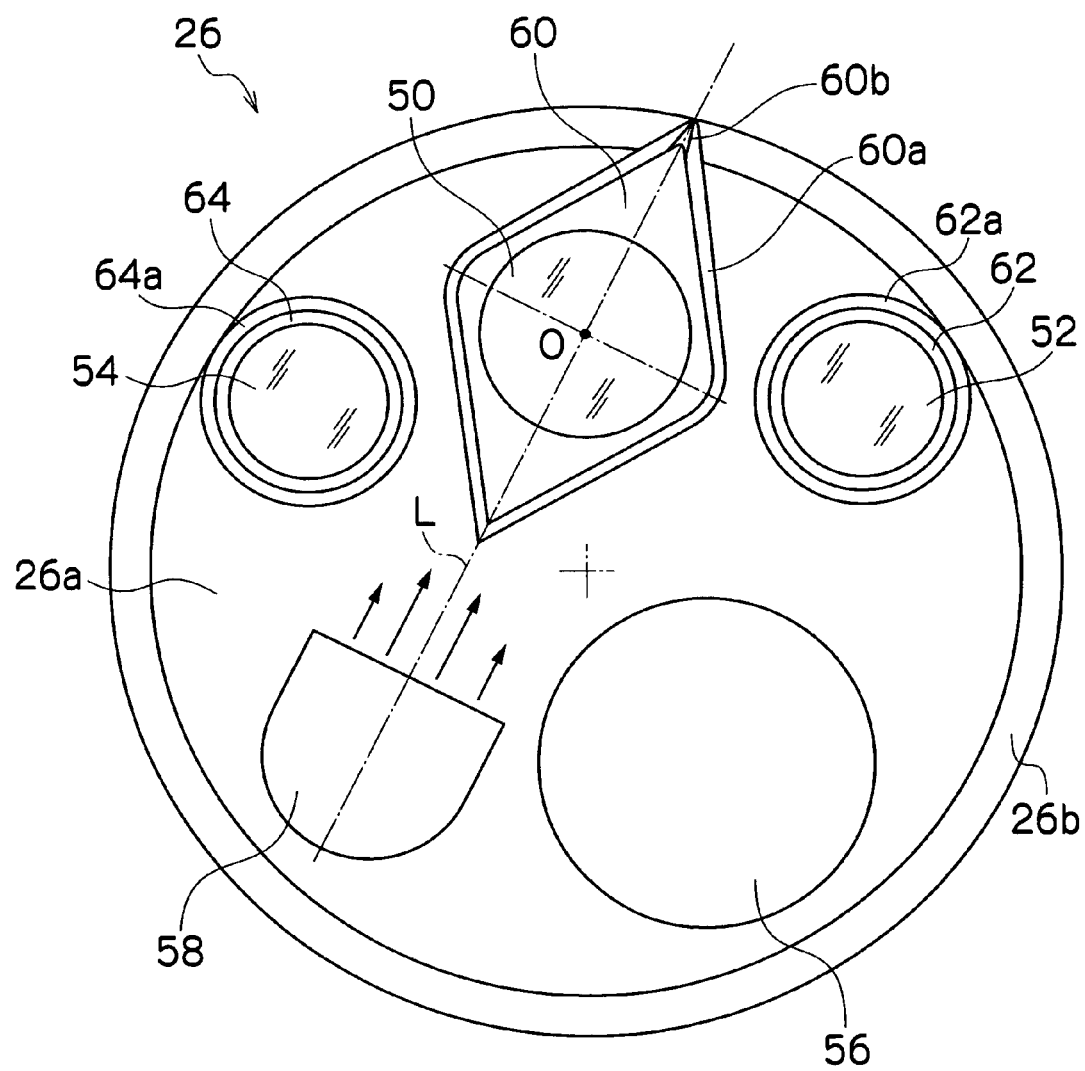
FIG. 6 is a front view illustrating a configuration of another embodiment of the distal end surface of the distal end part.
Figure 7:
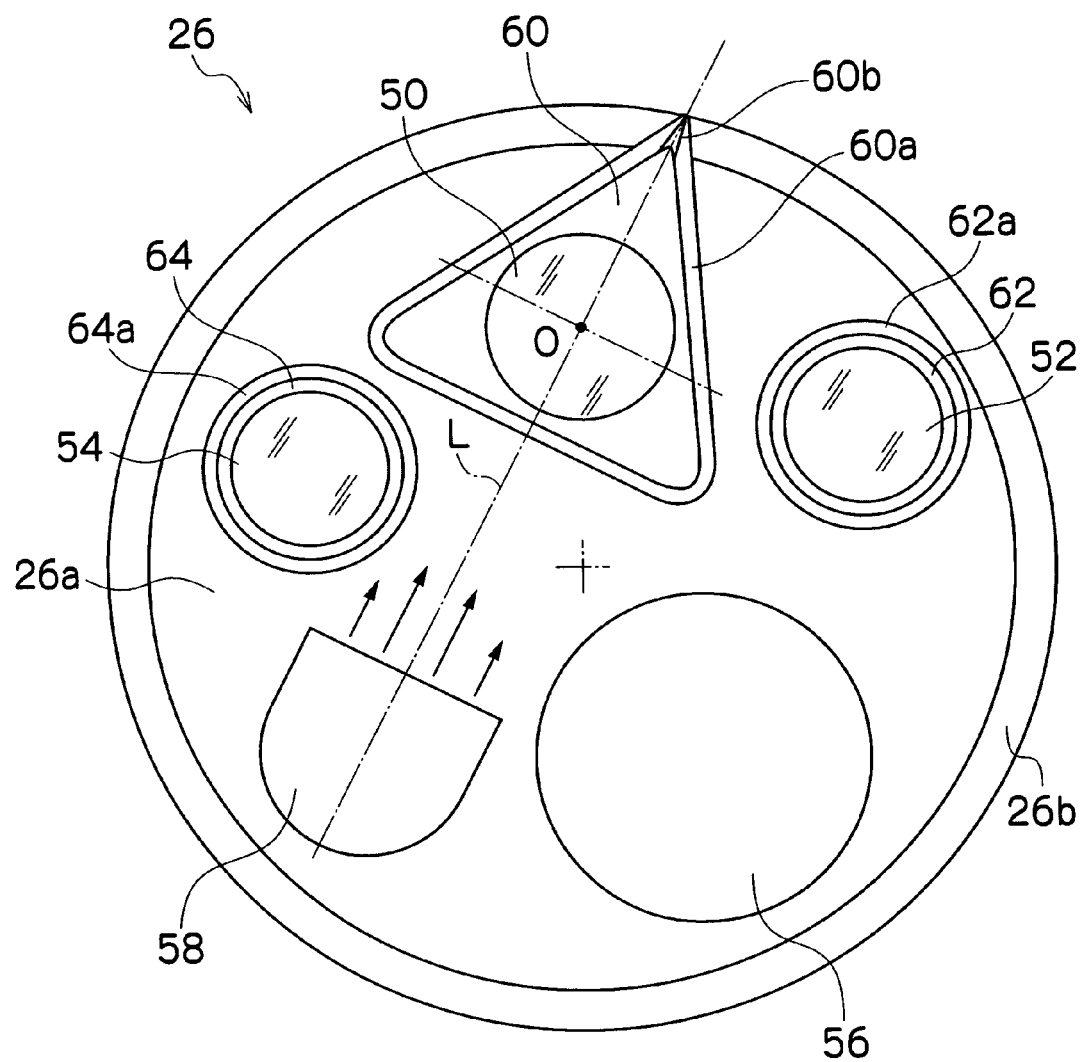
FIG. 7 is a front view illustrating a configuration of still another embodiment of the distal end surface of the distal end part.

In addition to the above-mentioned configuration, the outer peripheral shape of the observation window base part may be formed into a rhombic shape and a triangular shape as illustrated in FIGS. 6 and 7, respectively. In this way, the outer peripheral shape of the observation window base part is formed so as to converge toward at least the edge part 26*b* of the outer periphery of the distal end surface 26*a*, whereby it is possible to block the liquid flow having a low flow rate from flowing on the observation window 50, and to allow the cleaning liquid which has been used for cleaning to promptly move to the outside of the observation window 50. In addition, in this case, the converging end part 60*b* is round-chamfered at a diameter smaller than the round-chamfering diameter of the edge part 26*b* of the outer periphery of the distal end surface 26*a*, whereby it is possible to prevent the liquid drops from attaching to the edge part 26*b* in the vicinity of the observation window 50.

<Third Embodiment>

Figure 8:
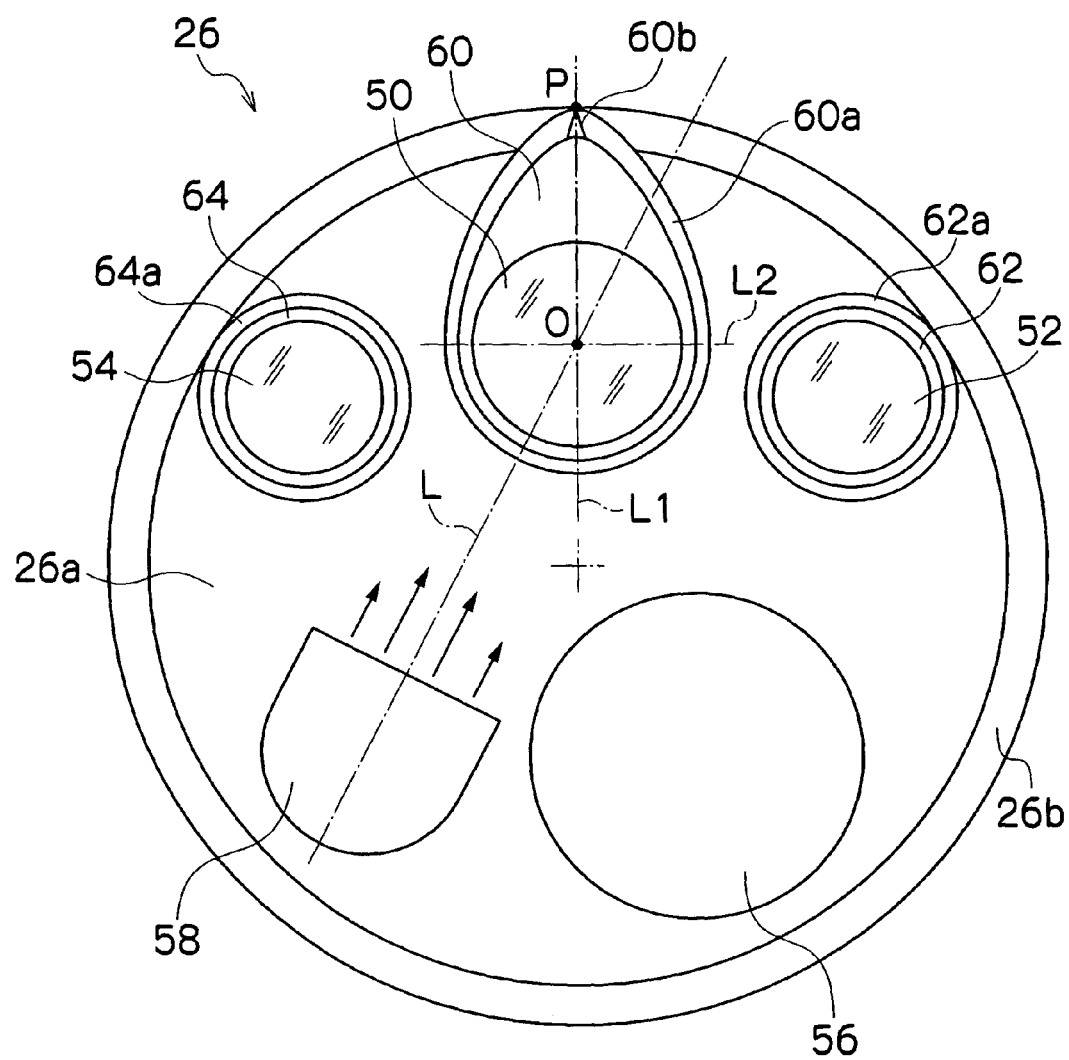
FIG. 8 is a front view illustrating a configuration of a third embodiment of the distal end surface of the distal end part.

FIG. 8 is a front view illustrating a configuration of a third embodiment of the distal end surface of the distal end part of the endoscope according to the presently disclosed subject matter.

As illustrated in FIG. 8, the endoscope of the present embodiment is different in a converging direction of the observation window base part 60 from the endoscope of the first embodiment. That is, the observation window base part 60 is formed so as to extend toward the edge part 26*b* located at the closest position from the observation window 50, and is formed so as to converge at the edge part 26*b* located at the closest position.

More specifically, the observation window base part 60 is formed symmetrically to a straight line L1 which connects the center O of the observation window 50 with a point P located at the closest position from the observation window 50, in the outer peripheral edge of the distal end surface 26*a* (a point whose distance from the outer peripheral part of the observation window 50 is the shortest). An outer shape of a region on the center side of the distal end surface 26*a* with respect to a straight line L2 is formed into a circle, and the straight line L2 passes through the center O of the observation window 50, and is orthogonal to the straight line L1. Further, an outer shape of a region on the outer peripheral side of the distal end surface 26*a* with respect to the straight line L2 (the region not facing the nozzle 58) is formed so as to extend toward the outer periphery of the distal end surface 26*a* and converge at the edge part 26*b* of the outer periphery of the distal end surface 26*a* (formed into airfoil section).

The observation window base part 60 of the endoscope of the present embodiment is the same as the observation window base part 60 of the endoscope of the first embodiment in that: the peripheral edge part 60*a* is formed so as to be inclined at a prescribed angle; the converging end part 60*b* is round-chamfered; and the round-chamfering diameter of the round-chamfered end part 60*b* is formed at a diameter smaller than the round-chamfering diameter of the similarly round-chamfered edge part 26*b* of the outer periphery of the distal end surface 26*a*.

In this way, the observation window base part 60 is converged toward the edge part 26*b* located at the closest position from the observation window 50, whereby it is possible to prevent the liquid drops from attaching to the edge part 26*b* in the vicinity of the observation window 50.

It should be noted that, although the observation window base part 60 is converged toward the edge part 26*b* located at the closest position in the present embodiment, it is preferable to adjust as appropriate the converging direction in accordance with the direction of the nozzle 58 (the jet direction of the cleaning fluid), a layout of another element, and the like. That is, it is preferable to converge the observation window base part 60 toward a more effective direction in consideration of various factors.

<Fourth Embodiment>

Figure 9:
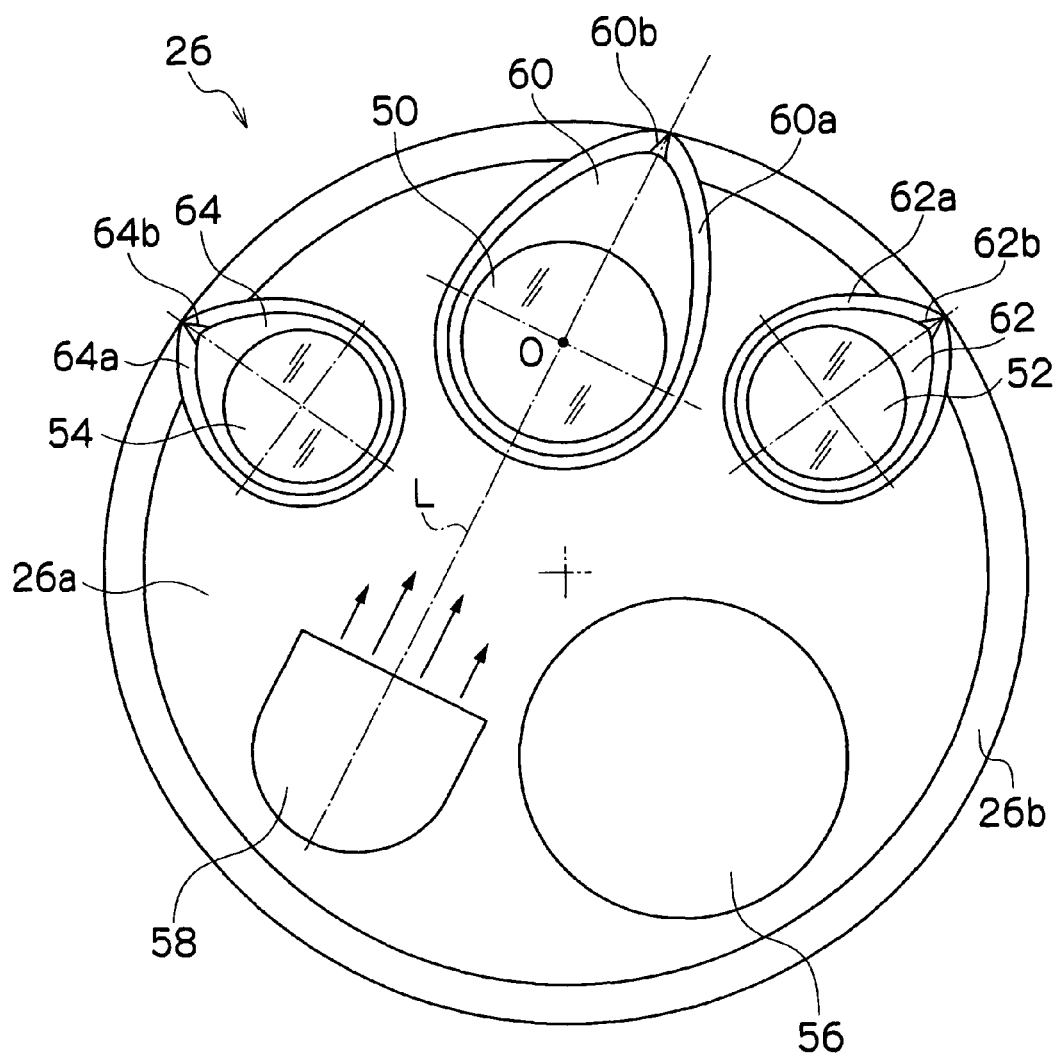
FIG. 9 is a front view illustrating a configuration of a fourth embodiment of the distal end surface of the distal end part.

FIG. 9 is a front view illustrating a configuration of a fourth embodiment of the distal end surface of the distal end part of the endoscope according to the presently disclosed subject matter.

As illustrated in FIG. 9, the endoscope of the present embodiment is different from the endoscope 1 of the first embodiment in that the outer peripheral shapes of the illumination window base parts 62 and 64 are also formed into a streamline shape.

In this way, the outer peripheral shapes of the illumination window base parts 62 and 64 are also formed into the streamline shape, whereby it is possible to prevent the liquid flow having a low flow rate from flowing on the illumination windows 52 and 54, and to promptly eliminate the liquid flow which has flown on the illumination windows 52 and 54 from the illumination windows 52 and 54.

In addition, similarly to the observation window base part 60, the illumination window base parts 62 and 64 are formed so as to extend toward the outer periphery of the distal end surface 26*a*, and are formed so as to converge at the edge part 26*b* of the outer periphery of the distal end surface 26*a*. End parts 62b and 64b of the illumination window base parts 62 and 64 are round-chamfered at a diameter smaller than the round-chamfering diameter of the edge part 26b. Accordingly, it is possible to prevent the liquid drops from attaching to the vicinities of the illumination windows 52 and 54.

Figure 10:
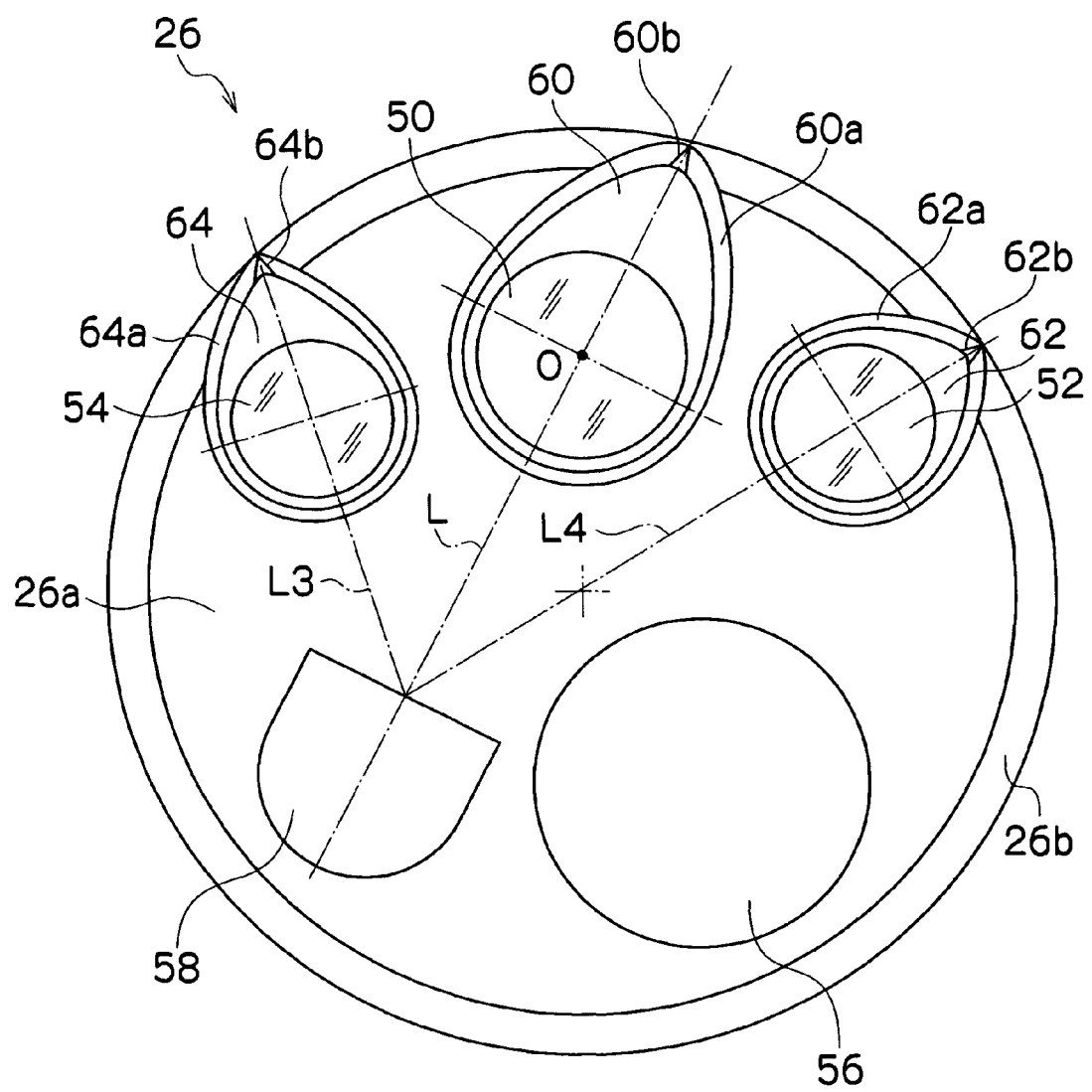
FIG. 10 is a front view illustrating a configuration of another embodiment of the distal end surface of the distal end part.

It should be noted that, in the present embodiment, although the illumination window base parts 62 and 64 are formed so as to extend toward respective portions of the edge part 26b located at the closest positions from the illumination windows 52 and 54 and converge at the respective portions of the edge part 26b, the respective converging directions thereof are not limited to this embodiment. For example, as illustrated in FIG. 10, the illumination window base parts 62 and 64 may be formed so as to extend along straight lines L3 and L4 which respectively connect the illumination windows 52 and 54 with the nozzle 58 and converge at the edge part 26b of the outer periphery of the distal end surface 26a. That is, in consideration of the flow of the cleaning fluid jetted from the nozzle 58, the converging parts of the illumination window base parts 62 and 64 may be formed so as to extend along the flow thereof.

<Fifth Embodiment>

Figure 11:
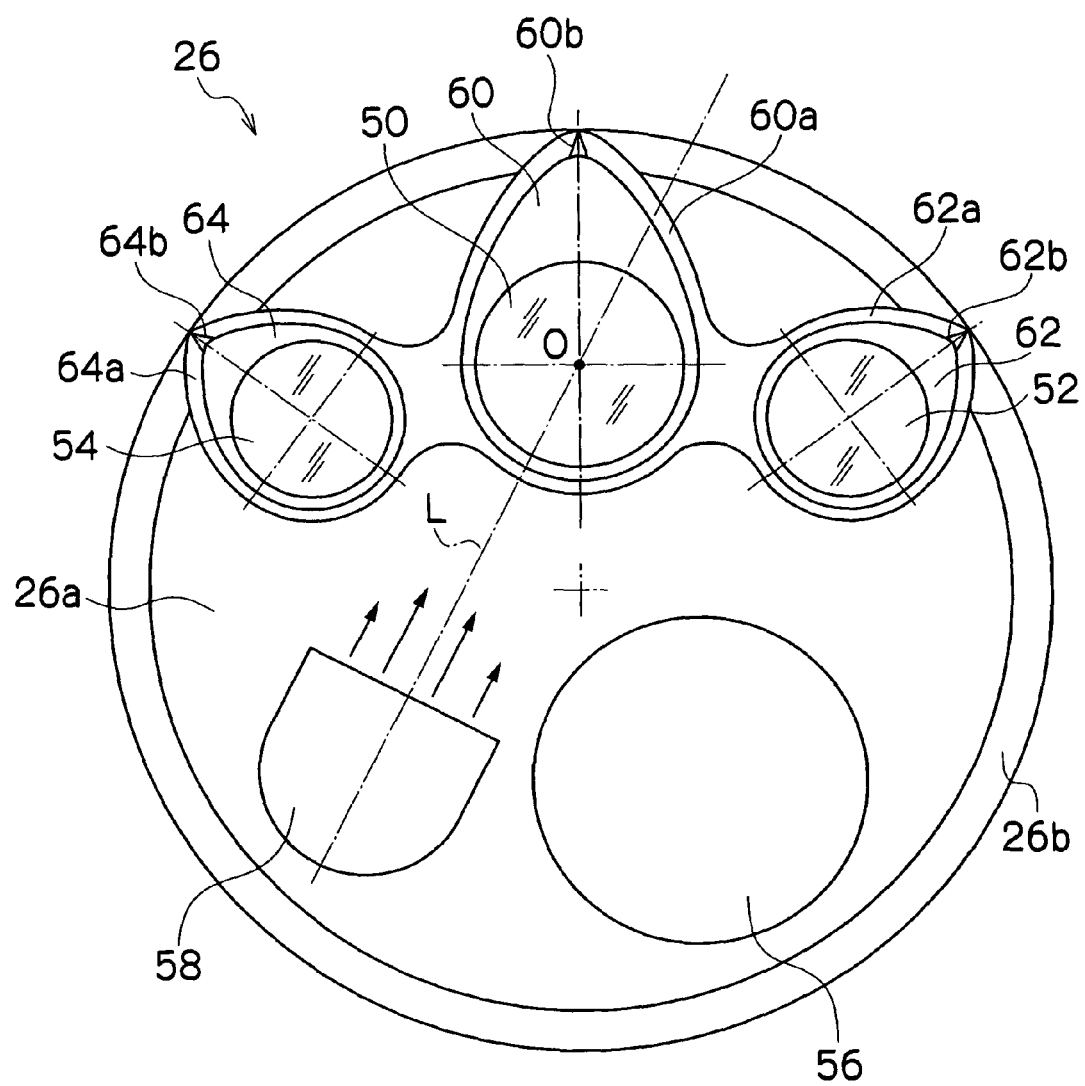
FIG. 11 is a front view illustrating a configuration of a fifth embodiment of the distal end surface of the distal end part.

FIG. 11 is a front view illustrating a configuration of a fifth embodiment of the distal end surface of the distal end part of the endoscope according to the presently disclosed subject matter.

As illustrated in FIG. 11, in the endoscope of the present embodiment, the observation window base part 60 and the illumination window base parts 62 and 64 are integrally formed into streamline shapes.

In this way, the observation window base part 60 and the illumination window base parts 62 and 64 may be integrally formed.

Figure 12:
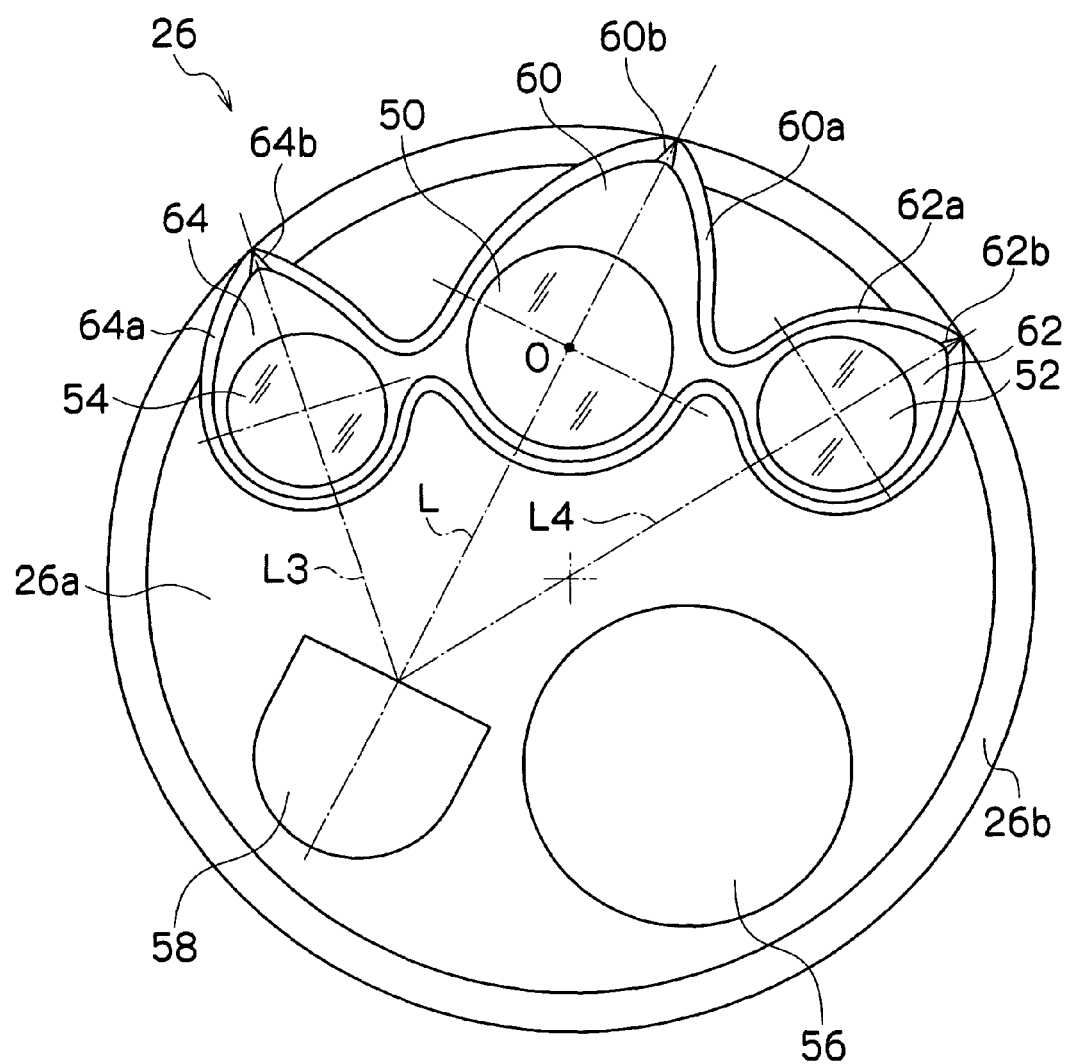
FIG. 12 is a front view illustrating a configuration of another embodiment of the distal end surface of the distal end part.

It should be noted that, in the embodiment illustrated in FIG. 11, the observation window base part 60 and the illumination window base parts 62 and 64 are formed so as to converge toward respective portions of the edge part 26b located at the closest position from the observation window 50, but the converging directions of the respective base parts are not limited thereto. In addition to the above-mentioned configuration, as illustrated in FIG. 12, in consideration of the flow of the cleaning fluid jetted from the nozzle 58, the respective base parts may be extended along the flow thereof and converged at the edge part 26b. That is, it is preferable that the converging directions of the observation window base part 60 and the illumination window base parts 62 and 64 be set to the most effective directions to eliminate the liquid drops in consideration of the flow of the cleaning fluid jetted from the nozzle 58, the layout, and the like.

What is claimed is:

1. An endoscope comprising:
    a distal end part having a flat end surface and a round-chamfered outer peripheral edge;
    an observation window base part formed on the flat end surface of the distal end part so as to protrude distally from the flat end surface;
    an observation window placed on the observation window base part; and
    a nozzle which jets a cleaning fluid toward the observation window, wherein:
    the observation window base part has an outer peripheral shape formed into a streamline shape with respect to a flow of the cleaning fluid jetted from the nozzle,
    the observation window base part is located on the distal end part such that a periphery portion of the observation window base part extends up to the outer peripheral edge of the distal end part along the flow of the cleaning fluid jetted from the nozzle, and
    the outer peripheral shape of the observation window base part decreases linearly in width from the observation window to the outer peripheral edge of the distal end part in a direction of flow of the cleaning fluid.

2. The endoscope according to claim 1, wherein the outer peripheral shape of the observation window base part is formed so as to converge towards the nozzle.

3. The endoscope according to claim 1, wherein an outer peripheral edge of the observation window base part is formed so as to be inclined.

4. The endoscope according to claim 1, further comprising:
    an illumination window base part formed on the flat end surface of the distal end part so as to protrude distally from the flat end surface; and
    an illumination window placed on the illumination window base part,
    wherein the illumination window base part has an outer peripheral shape formed into a streamline shape with respect to the flow of the cleaning fluid jetted from the nozzle.

5. The endoscope according to claim 4, wherein the illumination window base part is formed so as to extend up to the outer peripheral edge of the distal end part along the flow of the cleaning fluid jetted from the nozzle.

6. The endoscope according to claim 4, wherein an outer peripheral shape of the illumination window base part is formed so as to converge toward the outer peripheral edge of the distal end part.

7. The endoscope according to claim 6, wherein the outer peripheral shape of the illumination window base part is formed so as to converge toward the nozzle.

8. The endoscope according to claim 4, wherein an outer peripheral edge of the illumination window base part is formed so as to be inclined.

9. The endoscope according to claim 1, further comprising:
    an illumination window base part formed on the flat end surface of the distal end part so as to protrude distally from the flat end surface; and
    an illumination window placed on the illumination window base part,
    wherein the illumination window base part is formed so as to extend up to the outer peripheral edge of the distal end part along the flow of the cleaning fluid jetted from the nozzle.

10. The endoscope according to claim 1, further comprising:
    an illumination window base part formed on the flat end surface of the distal end part so as to protrude distally from the flat end surface; and
    an illumination window placed on the illumination window base part,
    wherein the illumination window base part is formed so as to extend up to the outer peripheral edge of the distal end part along a straight line which connects the nozzle with the illumination window.

11. The endoscope according to claim 1, further comprising:
    an illumination window base part formed on the flat end surface of the distal end part so as to protrude distally from the flat end surface; and
    an illumination window placed on the illumination window base part, wherein the illumination window base part is formed so as to extend up to the outer peripheral edge of the distal end part located at a closest position from the illumination window.

12. An endoscope comprising:
a distal end part having a flat end surface and a round-chamfered outer peripheral edge;
an observation window base part formed on the flat end surface of the distal end part so as to protrude distally from the flat end surface;
an observation window placed on the observation window base part; and
a nozzle which jets a cleaning fluid toward the observation window, wherein:
the observation window base part formed so as to extend up to the outer peripheral edge of the distal end part along a flow of the cleaning fluid jetted from the nozzle, and
an outer peripheral shape of the observation window base part decreases linearly in width from the observation window to the outer peripheral edge of the distal end part in a direction of flow of the cleaning fluid.

13. The endoscope according to claim 12, further comprising:
an illumination window base part formed on the flat end surface of the distal end part so as to protrude distally from the flat end surface; and
an illumination window placed on the illumination window base part,
wherein the illumination window base part has an outer peripheral shape formed into a streamline shape with respect to the flow of the cleaning fluid jetted from the nozzle.

14. The endoscope according to claim 12, wherein the outer peripheral shape of the observation window base part is formed into a rhombic shape.

15. The endoscope according to claim 12, wherein the outer peripheral shape of the observation window base part is formed into a triangular shape.

16. The endoscope according to claim 12, wherein the outer peripheral shape of the observation window base part is formed so as to converge towards the nozzle.

17. An endoscope comprising:
a distal end part having a flat end surface and a round-chamfered outer peripheral edge;
an observation window base part formed on the flat end surface of the distal end part so as to protrude distally from the flat end surface;
an observation window placed on the observation window base part; and
a nozzle which jets a cleaning fluid toward the observation window, wherein:
the observation window base part is formed so as to extend up to the outer peripheral edge of the distal end part along a straight line which connects the nozzle with the observation window, and
an outer peripheral shape of the observation window base part decreases linearly in width from the observation window to the outer peripheral edge of the distal end part in a direction of flow of the cleaning fluid.

18. The endoscope according to claim 17, further comprising:
an illumination window base part formed on the flat end surface of the distal end part so as to protrude distally from the flat end surface; and
an illumination window placed on the illumination window base part,
wherein the illumination window base part has an outer peripheral shape formed into a streamline shape with respect to the flow of the cleaning fluid jetted from the nozzle.

19. The endoscope according to claim 17, wherein the outer peripheral shape of the observation window base part is formed into a rhombic shape.

20. The endoscope according to claim 17, wherein the outer peripheral shape of the observation window base part is formed into a triangular shape.

21. The endoscope according to claim 17, wherein the outer peripheral shape of the observation window base part is formed so as to converge towards the nozzle.

22. An endoscope comprising:
a distal end part having a flat end surface and a round-chamfered outer peripheral edge;
an observation window base part formed on the flat end surface of the distal end part so as to protrude distally from the flat end surface;
an observation window placed on the observation window base part; and a nozzle which jets a cleaning fluid toward the observation window, wherein:
the observation window base part on has an outer peripheral shape formed into a streamline shape with respect to a flow of the cleaning fluid jetted from the nozzle,
the observation window base part is located on the distal end part such that a periphery portion of the observation window base part extends up to the outer peripheral edge of the distal end part along the flow of the cleaning fluid jetted from the nozzle,
the outer peripheral shape of the observation window base part is formed so as to converge on a convergence point at the outer peripheral edge of the distal end part to decrease monotonically in width from the observation window to the convergence point at the outer peripheral edge of the distal end part in a direction of flow of the cleaning fluid,
the outer peripheral shape of the observation window base part at the convergence point is sharper than the outer peripheral shape of the observation window base part around the convergence point, and
wherein the convergence point is aligned with a central axis of the nozzle and a central axis of the observation window.

23. The endoscope according to claim 22, wherein the outer peripheral shape of the observation window base part is formed into an airfoil section.

24. An endoscope comprising:
a distal end part having a flat end surface and a round-chamfered outer peripheral edge;
an observation window base part formed on the flat end surface of the distal end part so as to protrude distally from the flat end surface;
an observation window placed on the observation window base part; and
a nozzle which jets a cleaning fluid toward the observation window, wherein:
the observation window base part is formed so as to extend up to the outer peripheral edge of the distal end part along a flow of the cleaning fluid jetted from the nozzle,
an outer peripheral shape of the observation window base part is formed so as to converge on a convergence point at the outer peripheral edge of the distal end part to decrease monotonically in width from the observation window to the convergence point at the outer peripheral edge of the distal end part in a direction of flow of the cleaning fluid, the outer peripheral shape of the observation window base part at the convergence point is sharper than the outer peripheral shape of the observation window base part around the convergence point, and wherein the convergence point is aligned with a central axis of the nozzle and a central axis of the observation window.

25. The endoscope according to claim 24, wherein the outer peripheral shape of the observation window base part is formed into an airfoil section.

26. An endoscope comprising:

a distal end part having a flat end surface and a round-chamfered outer peripheral edge;

an observation window base part formed on the flat end surface of the distal end part so as to protrude distally from the flat end surface;

an observation window placed on the observation window base part; and a nozzle which jets a cleaning fluid toward the observation window, wherein:

the observation window base part is formed so as to extend up to the outer peripheral edge of the distal end part along a straight line which connects the nozzle with the observation window, an outer peripheral shape of the observation window base part is formed so as to converge on a convergence point at the outer peripheral edge of the distal end part to decrease monotonically in width from the observation window to the convergence point at the outer peripheral edge of the distal part in a direction of flow of the cleaning fluid, the outer peripheral shape of the observation window base part at the convergence point is sharper than the outer peripheral shape of the observation window base part around the convergence point, and wherein the convergence point is aligned with a central axis of the nozzle and a central axis of the observation window.

27. The endoscope according to claim 26, wherein the outer peripheral shape of the observation window base part is formed into an airfoil section.

* * * * *